(12) United States Patent
Baty et al.

(10) Patent No.: US 10,316,315 B2
(45) Date of Patent: Jun. 11, 2019

(54) METHODS FOR SELECTING BINDERS BY PHAGE DISPLAY AND MASKED SELECTION

(71) Applicants: INSERM (INSTITUT NATIONAL DE LA SANTE ET DE LA RECHERCHE MEDICALE), Paris (FR); UNIVERSITE D'AIX MARSEILLE, Marseilles (FR); INSTITUT JEAN PAOLI & IRENE CALMETTES, Marseilles (FR); CENTRE NATIONAL DE LA RECHERCHE SCIENTIFIQUE (CNRS), Paris (FR)

(72) Inventors: Daniel Baty, Marseilles (FR); Patrick Chames, Marseilles (FR)

(73) Assignees: INSERM (INSTITUT NATIONAL DE LA SANTE ET DE LA RECHERCHE MEDICALE), Paris (FR); UNIVERSITE D'AIX-MARSEILLE, Marseilles (FR); INSTITUT JEAN PAOLI & IRENE CALMETTES, Marseilles (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 229 days.

(21) Appl. No.: 15/427,126

(22) Filed: Feb. 8, 2017

(65) Prior Publication Data

US 2017/0175107 A1    Jun. 22, 2017

Related U.S. Application Data

(62) Division of application No. 14/403,228, filed as application No. PCT/EP2013/060786 on May 24, 2013, now Pat. No. 9,605,257.

(30) Foreign Application Priority Data

May 25, 2012   (EP) ..................................... 12305585

(51) Int. Cl.
    C40B 30/04     (2006.01)
    C12N 15/10     (2006.01)

(52) U.S. Cl.
    CPC .......... *C12N 15/1037* (2013.01); *C40B 30/04* (2013.01)

(58) Field of Classification Search
    None
    See application file for complete search history.

(56) References Cited

PUBLICATIONS

Arbabi-Ghahroudi et al. (2009) Bacteriophages Methods and Protocols vol. 2 pp. 341 to 364.*

* cited by examiner

*Primary Examiner* — Christian C Boesen
(74) *Attorney, Agent, or Firm* — W&C IP

(57) ABSTRACT

The present invention relates to methods for selecting binders by phage display and masked selection. More particularly, the present invention relates to a method for selecting a plurality of binders specific for at least one relevant target comprising screening a phage binder library of binders against the relevant target in presence of a plurality of binders obtained from a library of binders directed against at least one irrelevant target and positively selecting the binders that are specific for the at least one relevant target.

2 Claims, 10 Drawing Sheets

Figure 1A:
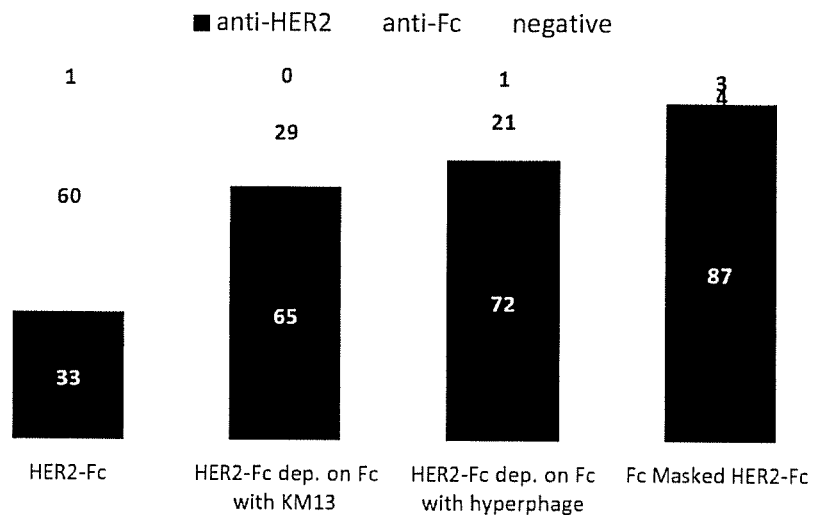

| sdAb | $K_D$ (nM) |
|------|-----------|
| A.A10 | 2.7 |
| A.F1 | 2.2 |
| A.B5 | 3.2 |
| A.E4 | 1.9 |
| A.D6 | 7.3 |
| A.H10 | 7 |
| C.A5 | 2.4 |
| C.E4 | 0.5 |
| C.D4 | 2 |
| C.G5 | 2.3 |
| C.E10 | 4.7 |
| H.H8 | 5.3 |

| sdAb | $K_D$ (nM) |
|------|------------|
| E1   | 6.1        |
| H4   | 0.7        |
| A3   | 9.2        |
| A4   | 0.6        |
| D4   | 3.4        |
| F5   | 0.3        |
| G4   | 0.4        |

|  | - | + | ++ | +++ |
|---|---|---|---|---|
| M.H12 | 2% | 12% | 40% | 46% |
| M.H3 | 21% | 46% | 25% | 8% |
Figure 5C
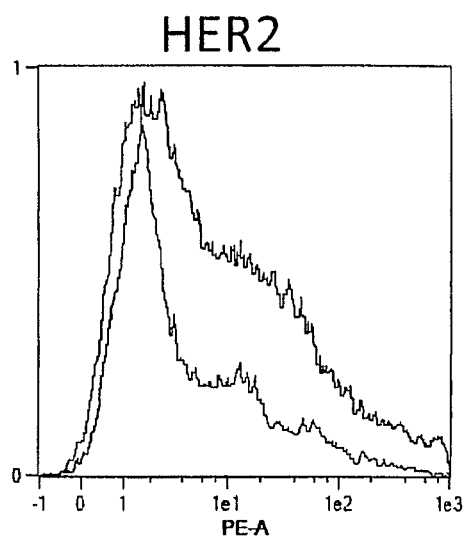
Figure 6A
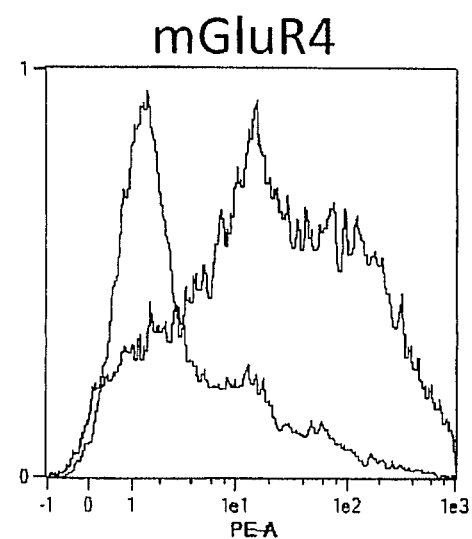
Figure 6B

METHODS FOR SELECTING BINDERS BY PHAGE DISPLAY AND MASKED SELECTION

CROSS-REFERENCE TO RELATED APPLICATIONS

This application is a divisional application of U.S. Ser. No. 14/403,228, filed Nov. 24, 2014, now U.S. Pat. No. 9,605,257, which itself was a national stage filing under Rule 371 from PCT/EP2013/060786 filed May 24, 2013 which claimed priority to European Application 12305585.7 filed May 25, 2012.

FIELD OF THE INVENTION

The present invention relates to methods for selecting binders by phage display and masked selection.

BACKGROUND OF THE INVENTION

Hybridoma [1] and phage-display recombinant antibody systems [2] are currently the predominant methods for isolating monoclonal Abs. Display of recombinant antibodies (Ab) on the surface of bacteriophage M13 has numerous advantages compared to conventional hybridoma technology. When combined with the use of large non-immune libraries, phage Ab selection represents a rich source of binders that can be isolated in a fraction of the time needed for hybridoma-based approaches. As an in vitro selection methods, it permits the selection of binders against toxic or highly conserved antigens, which is not easily performed using the conventional hybridoma techniques and importantly, it can be used to isolate fully human antibody fragments [3]. Consequently, phage display rapidly became an established procedure for the isolation of binders against a wide variety of antigens.

Phage display-based antibody isolation typically relies on the use of recombinant proteins for several steps, including immunizations (if needed), library enrichment by selection on immobilized antigen, screening, and characterization of antibodies specificity and affinity [4]. This procedure is efficient but depends on the availability of purified recombinant proteins. Unfortunately, some surface molecules, such as G-protein coupled receptors, cannot be easily expressed and purified in a native conformation. Some molecules with large extracellular domains may adopt a specific conformation due to interaction with other cell surface proteins, thereby forming complexes that are cumbersome to produce by recombinant expression. Moreover, many standard screening practices, such as the adsorption of recombinant proteins on plastic, may significantly alter protein conformations [5]. For these reasons, Abs selected on the basis of binding to a recombinant protein may not bind the native conformation of this protein. It is thus of high interest to develop procedures entirely based on the use of intact cells expressing the receptor of choice. However, in this case, an extra step is necessary to enrich for phage-Abs binding to the receptor of interest rather than to other cell surface proteins. Since selection steps are performed in vitro, it is possible to influence the outcome of a selection by performing some additional steps such as deletion steps (also named negative selection) prior to positive selections to remove unwanted specificities or cross-reactions [6], or competitive elution using a ligand or an antibody to favor the selection of binders against a precise epitope [7].

Along this line, it would be of very high interest to establish a procedure able to reliably guide the selection toward an unknown but relevant antigen within a complex mixture, such as a tumor maker overexpressed at the surface of intact cells, or in a cell lysate. Indeed, during the past two decades, there has been a growing interest in approaches aiming at discovering new diagnosis biomarkers and identifying new potential surface markers for targeted therapy. Several studies have described the use of phage display and libraries of recombinant antibodies for the isolation of tumor specific binders [8-14], leading in some cases to the identification of new tumor markers [15, 16]. Most of these strategies are based on the use of depletion steps on normal samples followed by a selection step on the tumor sample. Unfortunately, this procedure often leads to inconsistent results and its efficiency can be a limiting factor in complex situation such as the selection of antibodies against unknown overexpressed tumor antigens.

SUMMARY OF THE INVENTION

The present invention relates to methods for selecting binders by phage display and masked selection.

DETAILED DESCRIPTION OF THE INVENTION

The inventors have designed a new selection method, named masked selection that is relying on the blockade of unwanted epitopes to favor the accessibility of relevant ones. They demonstrate the efficiency of this method by selecting binders against a specific portion of a fusion protein, by selecting binders against a member of the seven transmembrane receptor family and a tyrosine kinase receptor using intact transfected HEK cells, or by selecting binders against unknown breast cancer markers not expressed on normal samples, as shown by flow cytometry and immunohistochemistry. The universality and efficiency of this approach should ultimately lead to the rapid selection of specific binders and the development of diagnostic and targeted therapies in various settings.

The present invention thus relates to a method for selecting a plurality of binders specific for at least one relevant target comprising screening a phage binder library of binders against the relevant target in presence of a plurality of binders obtained from a library of binders directed against at least one irrelevant target and positively selecting the binders that are specific for the at least one relevant target.

As used herein, the term "binder" refers to any kind of antibody fragments (scFv, Fab fragments), alternative scaffolds (darpins, monobodies, affibodies, anticalins) or peptides.

In one embodiment, the binders are single domain antibodies (sdAbs). The term "single domain antibody" (sdAb) or "VHH" refers to the single heavy chain variable domain of antibodies of the type that can be found in Camelid mammals which are naturally devoid of light chains. Such VHH are also called "nanobody®". According to the invention, sdAb can particularly be llama sdAb.

Typically, the libraries of binders (e.g. antibodies) according to the invention are generated after immunization with the relevant or irrelevant target(s) as described in the EXAMPLE.

In one embodiment, the relevant target consists of a protein of surface (e.g. a receptor protein) or a portion thereof (e.g. ectodomain of the protein).

For example, the protein may be specific for an immune cell regulatory molecule such as CD3, CD4, CD8, CD25, CD28, CD26, CTLA-4, ICOS, or CD11a. Other suitable protein include but are not limited to those associated with immune cells including T cell-associated molecules, such as TCR/CD3 or CD2; NK cell-associated targets such as NKG2D, FcγRIIIa (CD16), CD38, CD44, CD56, or CD69; granulocyte-associated targets such as FcγRI (CD64), FcαRI (CD89), and CR3 (CD11b/CD18); monocyte/macrophage-associated targets (such as FcγRI (CD64), FcαRI (CD89), CD3 (CD11b/CD18), or mannose receptor; dendritic cell-associated targets such as FcγRI (CD64) or mannose receptor; and erythrocyte-associated targets such as CRI (CD35).

Alternatively, the protein of surface is a cancer antigen. Known cancer antigens include, without limitation, c-erbB-2 (erbB-2 is also known as c-neu or HER-2), which is particularly associated with breast, ovarian, and colon tumor cells, as well as neuroblastoma, lung cancer, thyroid cancer, pancreatic cancer, prostate cancer, renal cancer and cancers of the digestive tract. Another class of cancer antigens is oncofetal proteins of nonenzymatic function. These antigens are found in a variety of neoplasms, and are often referred to as "tumor-associated antigens." Carcinoembryonic antigen (CEA), and α-fetoprotein (AFP) are two examples of such cancer antigens. AFP levels rise in patients with hepatocellular carcinoma: 69% of patients with liver cancer express high levels of AFP in their serum. CEA is a serum glycoprotein of 200 kDa found in adenocarcinoma of colon, as well as cancers of the lung and genitourinary tract. Yet another class of cancer antigens is those antigens unique to a particular tumor, referred to sometimes as "tumor specific antigens," such as heat shock proteins (e.g., hsp70 or hsp90 proteins) from a particular type of tumor. Other targets include the MICA/B ligands of NKG2D. These molecules are expressed on many types of tumors, but not normally on healthy cells. Additional specific examples of cancer antigens include epithelial cell adhesion molecule (Ep-CAM/TACSTD1), mesothelin, tumor-associated glycoprotein 72 (TAG-72), gp100, Melan-A, MART-1, KDR, RCAS1, MDA7, cancer-associated viral vaccines (e.g., human papillomavirus antigens), prostate specific antigen (PSA, PSMA), RAGE (renal antigen), CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), cancer-associated ganglioside antigens, tyrosinase, gp75, C-myc, Mart1, MelanA, MUM-1, MUM-2, MUM-3, HLA-B7, Ep-CAM, tumor-derived heat shock proteins, and the like (see also, e.g., Acres et al., Curr Opin Mol Ther 2004 February, 6:40-7; Taylor-Papadimitriou et al., Biochim Biophys Acta. 1999 Oct. 8; 1455(2-3):301-13; Emens et al., Cancer Biol Ther. 2003 July-August; 2(4 Suppl 1):S161-8; and Ohshima et al., Int J Cancer. 2001 Jul. 1; 93(1):91-6). Other exemplary cancer antigen targets include CA 195 tumor-associated antigen-like antigen (see, e.g., U.S. Pat. No. 5,324,822) and female urine squamous cell carcinoma-like antigens (see, e.g., U.S. Pat. No. 5,306,811), and the breast cell cancer antigens described in U.S. Pat. No. 4,960,716.

The protein may also be a receptor protein such as receptors associated with cancer progression (e.g., one of the HER1-HER4 receptors).

In one embodiment, the relevant target may be a carbohydrate antigen present at the surface of a cell (e.g. a cancer cell). For example the target may be selected from glycosylation groups of antigens that are preferentially produced by transformed (neoplastic or cancerous) cells, infected cells, and the like (cells associated with other immune system-related disorders). In one aspect, the antigen is a tumor-associated antigen. In an exemplary aspect, the antigen is O-acetylated-GD2 or glypican-3. In another particular aspect, the antigen is one of the Thomsen-Friedenreich (TF) antigens (TFAs).

In a further aspect, the present invention relates to a method for selecting a plurality of binders specific for a relevant polypeptide comprising i) building a binder library by using PBMCs obtained from at least one animal immunized with a fusion protein consisting of the relevant polypeptide fused to an irrelevant polypeptide ii) producing a phage binder library by infecting the binder library of step i) with a helper phage iii) performing with the phage binder library of step ii) at least one round of selection against the irrelevant polypeptide iv) producing soluble binders with the selected clones obtained at step iii)

v) performing with the phage binder library of step ii) at least one round of selection against the fusion protein of step i) in the presence of an excess of binders produced by step iv)

iv) cloning, recovering and optionally sequencing the binders from the clones selected at step v).

Methods for producing a phage binder library (e.g. a phage antibody library) are well known in the art and are typically described in the EXAMPLE. Typically, the helper phage is selected among any phage well known for phage display and include for example KM13 or Hyperphage (Progen biotechnik) helper phage such as described in the example.

In one embodiment, the fusion protein is built so as to solubilise the relevant polypeptide (e.g. ectodomain of cell surface protein of interest) and typically may consist of the relevant polypeptide fused to the Fc domain of an immunoglobulin (e.g. IgG1). Accordingly the irrelevant polypeptide is the Fc domain og the immunoglobulin.

In a further aspect, the present invention relates to a method for selecting a plurality of binders specific for a cell surface protein comprising i) providing a cell that was genetically transformed so as to express at its surface the cell surface protein ii) building a binder library by using PBMCs obtained from at least one animal immunized with the cell of step i)

iii) producing a phage binder library by infecting the binder library of step ii) with a helper phage iv) performing with the phage binder library of step ii) at least one round of selection against the cell of step i) that was not genetically transformed v) producing soluble binders with selected clones obtained at step iv)

vi) performing with the phage binder library of step iii) at least one round of selection against the cell of step i) in the presence of an excess of binders produced by step v)

vii) cloning, recovering and optionally sequencing the binders from the clones selected at step vi).

According to the invention, the cell is an eukaryotic cell. Preferably said cell is a mammalian cell. Typically said mammalian cells include but are not limited to cells from humans, dogs, cats, cattle, horses, sheep, pigs, goats, and rabbits. In a particular embodiment the cell is a human cell. In another particular embodiment said cell is a cell line. (e.g. HEK) In particular embodiment, the cell is a tumor cell obtainable from a patient.

The term "transformation" means the introduction of a "foreign" (i.e. extrinsic or extracellular) gene, DNA or RNA sequence to a host cell, so that the host cell will express the introduced gene or sequence to produce the desired protein coded by the introduced gene or sequence. A host cell that receives and expresses introduced DNA or RNA bas been "transformed". Typically, said transformation may be performed by using any vector well known in the art. Examples of suitable vectors include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+cells, 293 cells, etc. Detailed protocols for producing such replication-defective recombinant viruses may be found for instance in WO 95/14785, WO 96/22378, U.S. Pat Nos. 5,882,877, 6,013,516, 4,861,719, 5,278,056 and WO 94/19478.

According to the invention, any eukaryotic cell may be used. Preferably said cell is a mammalian cell. Typically said mammalian cells include but are not limited to cells from humans, dogs, cats, cattle, horses, sheep, pigs, goats, and rabbits. In a particular embodiment the cell is a human cell. In particular embodiment, the cell is a tumor cell obtainable from a patient. In another particular embodiment said cell is a cell line.

In a further aspect, the present invention relates to a method for selecting a plurality of binders specific for a cell comprising
i) building a binder library by using PBMCs obtained from at least one animal immunized with the cell or a cell lysate
ii) producing a phage binder library by infecting the binder library of step i) with a helper phage
iii) performing with the phage binder library of step ii) at least one round of selection against a second cell or second cell lysate
iv) producing soluble binders with selected clones obtained at step iii)
v) performing with the phage binder library of step iv) at least one round of selection against the cell in the presence of an excess of binders produced by step iv)
vi) cloning, recovering and optionally sequencing the binders from the clones selected at step v).

In a particular embodiment, the cell is also a eukaryotic cell as above described.

In one embodiment the cell is specific for a tissue and the second cell is specific for another type of tissue. In this case the method will be particularly suitable for providing a plurality of antibodies that may be used for diagnosing purpose or imaging purpose.

In one embodiment, the cell is a cancer cell and the second cell according to step iii) is a normal cell (i.e. the same type of cell that was not malignant transformed). The cancer cell may be isolated from a biopsy. The cancer may be selected from any cancer (e.g. breast cancer). In this case, the method of the invention will be particularly suitable for providing a set of antibodies specific for cancer antigens. Thereafter said antibodies may be useful for screening and identifying relevant cancer antigens that can represent relevant therapeutic targets or relevant diagnostic markers.

Accordingly, the present invention also relates to a method for selecting a plurality of binders with cancer specificity comprising i) building a binder library by using PBMCs obtained from at least one animal immunized with a mixture of cancer biopsy lysates
ii) producing a phage binder library by infecting the binder library of step i) with a helper phage
iii) performing with the phage binder library of step ii) at least one round of selection against a mixture of normal biopsy lysate
iv) producing soluble binders with selected clones obtained at step iii)
v) performing with the phage binder library of step ii) at least one round of selection against the mixture of cancer biopsy lysates in the presence of an excess of binders produced by step iv)
vi) cloning, recovering and optionally sequencing the binders from the clones selected at step v).

The present invention also relates to a method for selecting a plurality of binders with cancer specificity comprising
i) building a binder library by using PBMCs obtained from at least one animal immunized with a mixture of cancer cell lines
ii) producing a phage binder library by infecting the binder library of step i) with a helper phage
iii) performing with the phage binder library of step ii) at least one round of selection against a normal cell line
iv) producing soluble binders with selected clones obtained at step iii)
v) performing with the phage binder library of step ii) at least one round of selection against the mixture of cancer cell lines in the presence of an excess of binders produced by step iv)
vi) cloning, recovering and optionally sequencing the binders from the clones selected at step v).

The invention will be further illustrated by the following figures and examples. However, these examples and figures should not be interpreted in any way as limiting the scope of the present invention.

FIGURES

FIG. 1A and B: A) phage ELISA assay of clones selected on recombinant antigen. 94 clones randomly picked from each type of selection were assayed by monoclonal phage ELISA for binding to HER2-Fc, or Fc. Clones yielding a positive signal on HER2-Fc but not on Fc were considered anti-HER2. Those positive on HER2-Fc and Fc were considered anti-Fc and those negative on both were considered non binders (negative). Dep: depletion. Fc Masked: selection done in the presence of masking sdAbs B) Phage ELISA on cells using clones selected on transfected cells. 94 clones randomly picked from each type of selection were assayed by monoclonal phage ELISA for binding to HEK cells, HEK cells transfected with HER2 (HEK-HER2) or cells transfected with mGluR4. Binders yielding signals on transfected cells (HEK-HER2 or HEK-mGluR2) but not on HEK cells were considered receptor-specific (anti-Receptor), those yielding signal on all type of HEK cells were considered HEK-specific (anti-HEK) and those negative on all cells were considered negative. Sel.: selection.

Figure 2A:
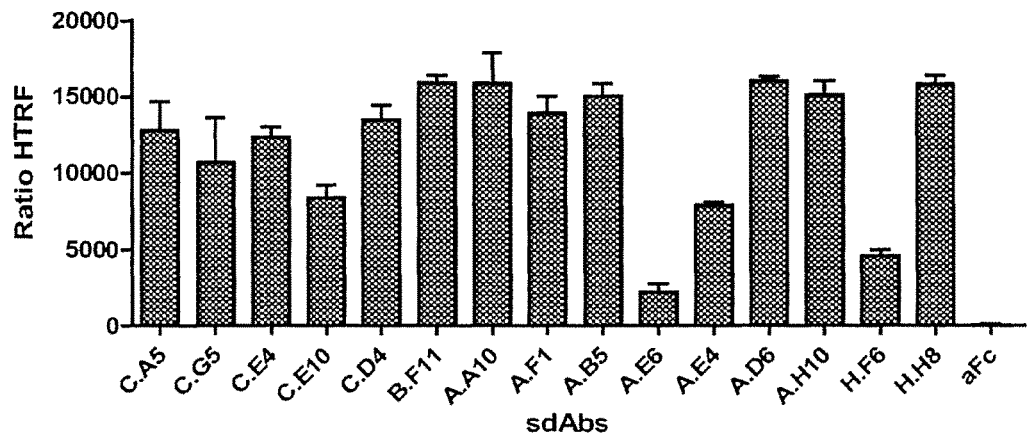
Figure 2B:
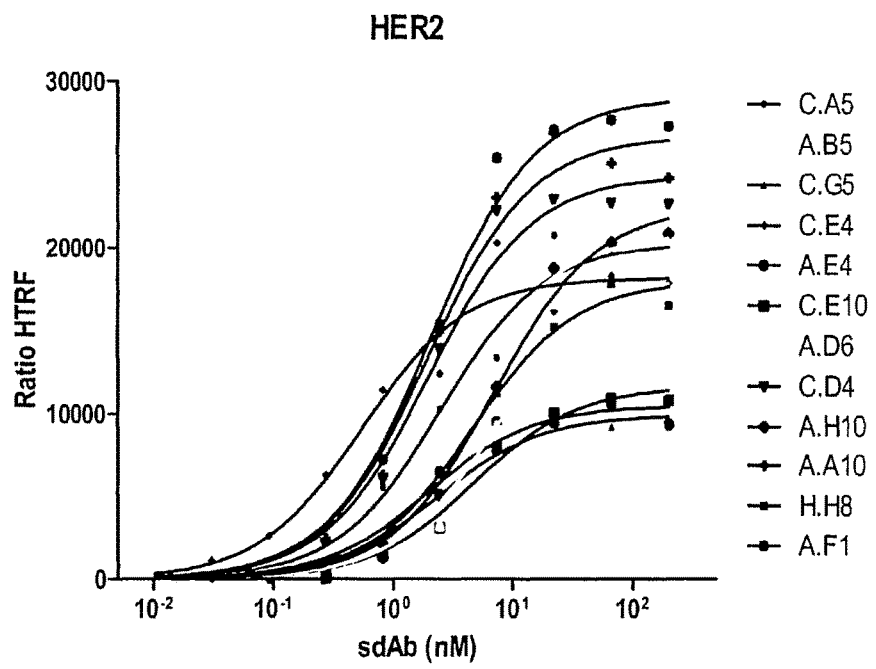
Figures 2C, 3A:
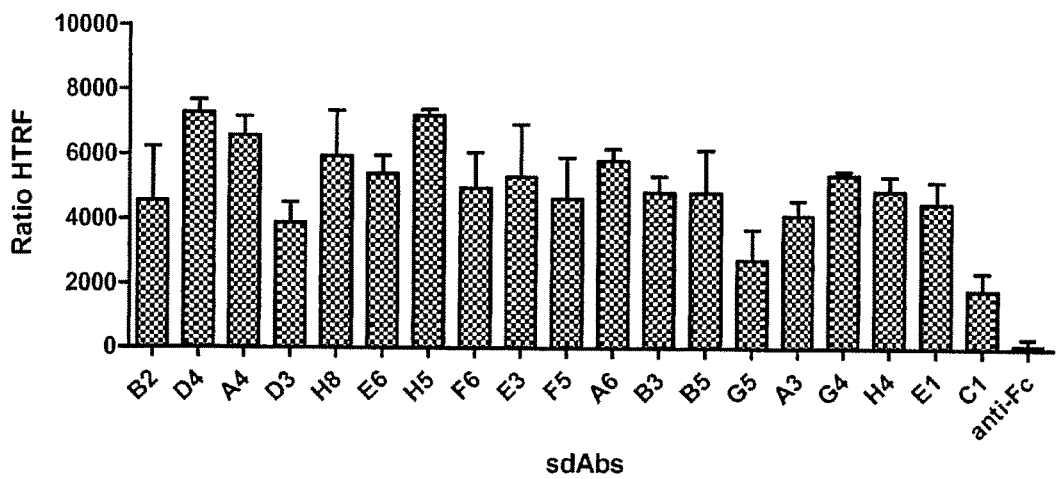

FIG. 2A-C: Characterization of anti-HER2 sdAbs by homogeneous time resolved fluorescence (HTRF) technology. A) Cells transfected by SNAP-tag HER2 and labeled with donor fluorophore were incubated with sdAbs and acceptor-labeled anti-6his mAb. The sdAb binding, detected by FRET, is expressed as HTRF ratio to normalize results for the HER2 receptor density (see Materials and Methods). B) Various concentrations of sdAbs were incubated on transfected and labeled cells and binding was followed by FRET as for A). C) Dissociation constants were calculated using a non-linear curve fitting software (Prism, GraphPad).

Figures 3B, 3C:
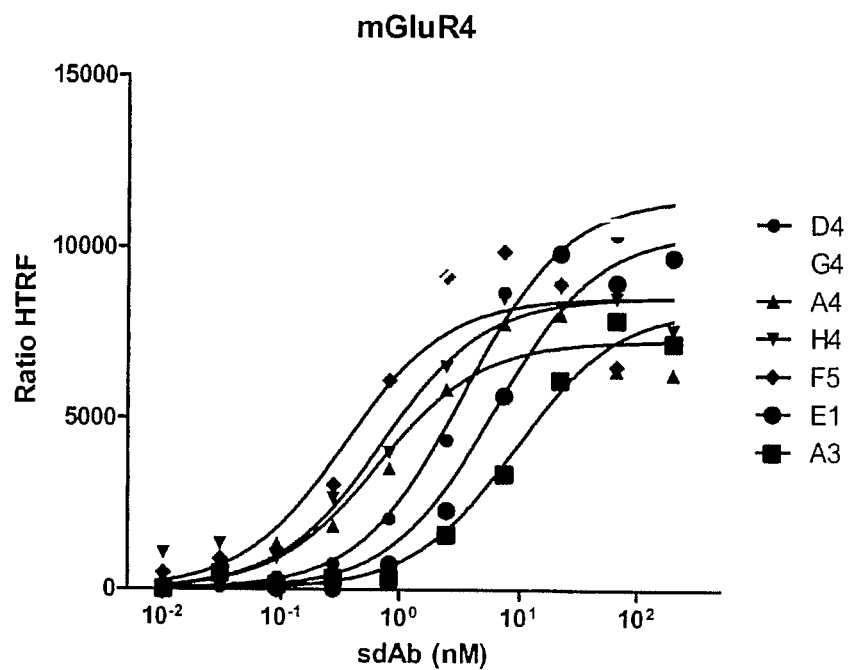

FIG. 3A-C: Characterization of anti-mGluR4 sdAbs by homogeneous time resolved fluorescence (HTRF) technology. SdAb targeting mGluR4 were characterized as described in FIG. 2. A). Cells transfected by SNAP-tag mGluR4 and labeled with donor fluorophore were incubated with sdAbs and acceptor-labeled anti-6his mAb. The sdAb binding, detected by FRET, is expressed as HTRF ratio to normalize results for the mGluR4 receptor density (see Materials and Methods). B) Various concentrations of sdAbs were incubated on transfected and labeled cells and binding was followed by FRET as for A). C) Dissociation constants were calculated using a non-linear curve fitting software (Prism, GraphPad).

Figure 4A:
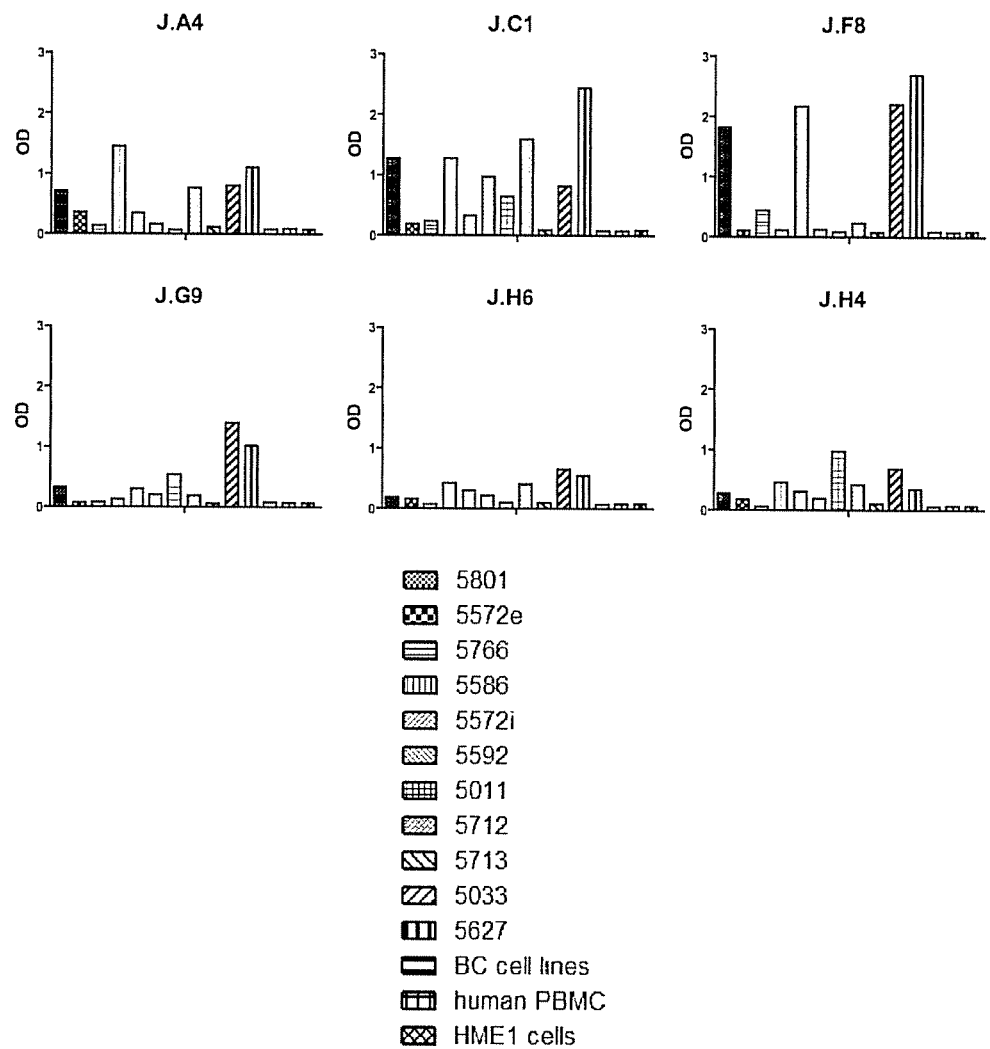
Figures 4B, 4C:
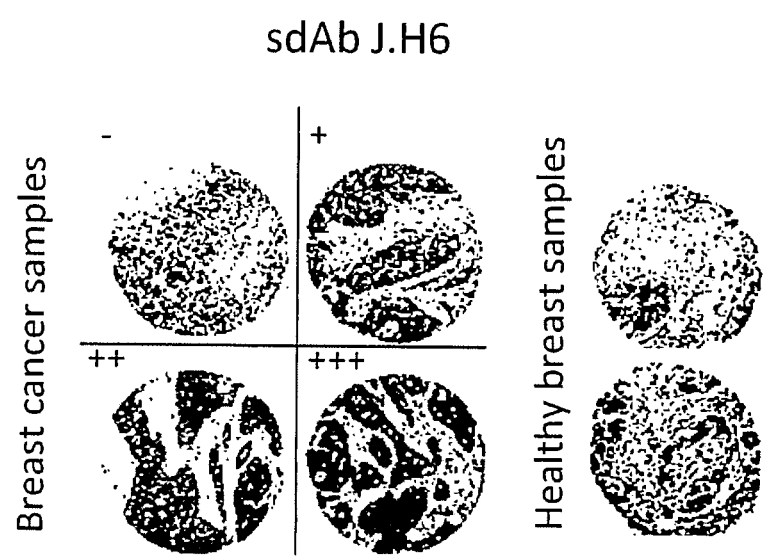

FIG. 4A-C: Fine characterization of candidate sdAbs isolated against biopsy lysates. A) Reverse phase phage-ELISA. Various biopsy lysates, a mixture of breast cancer cell lysates, (BC cell lines), a human PBMC lysate, and a healthy breast epithelial cell line HME1 lysate were coated on maxisorp. Phage-sdAbs were incubated and washed. Bound phage were detected using HRP-conjugated anti-M13 mAb. B) Tissue micro array analysis. Paraffin embedded slide containing 80 breast cancer samples or 14 healthy breast samples were incubated with purified and in vitro biotinylated sdAb J.H6. Bound sdAbs were detected using HRP-conjugated streptavidin. Representative examples are shown. C) Staining results were classified according to their intensity.

Figure 5A:
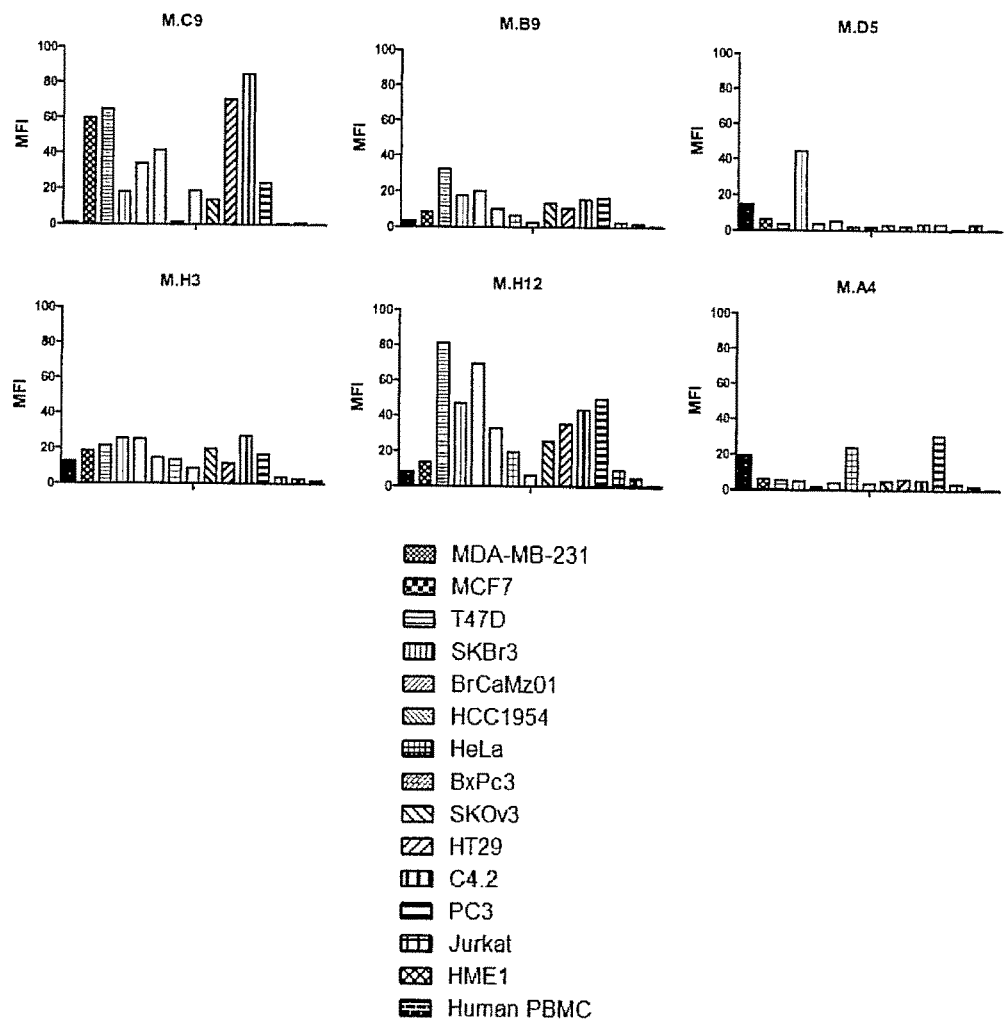
Figure 5B:
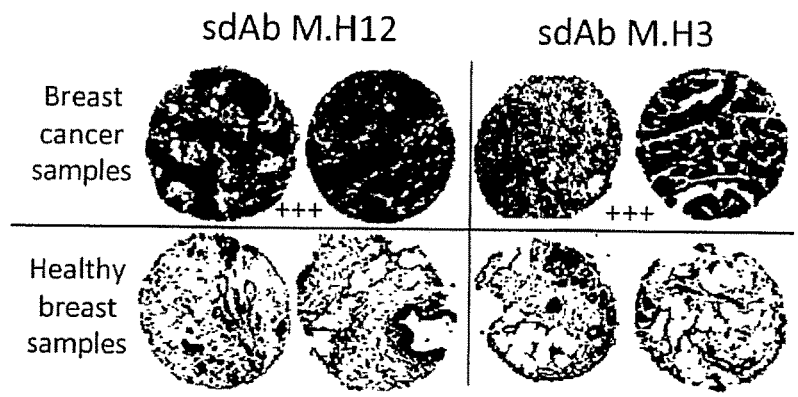

FIG. 5A-C: Fine characterization of candidate sdAbs against intact breast cancer cells. A) A phage cytometry assay was performed on 6 breast cancer cell lines, 7 cancer cell lines of various origins (cervical, pancreas, ovarian, colon, prostate, lymphocyte), on human PBMC and normal breast epithelium cell line HMEI. In vitro biotinylated sdAb were added on cells. After washing, bound sdAbs were detected with HRP-conjugated streptavidin. B) Tissue micro array analysis. Paraffin embedded tissue array containing 80 breast cancer samples and 14 healthy breast samples were incubated with in vitro biotinylated sdAbs. Bound sdAbs were detected by HRP-conjugated streptavidin. Shown are representative examples. C) Staining results were classified according to their intensity.

FIGS. 6A and B: Transfection level. Expression HER2 or mGluR4 (fused to SNAP and Flag tag) on the surface of HEK cells was followed by flow cytometry. A) HER2-transfected HEK cells (HEK-HER2) and B, mGluR4-transfected HEK cells (HEK-mGLuR4) were incubated with anti-Flag mAb (black line) or not (gray line). Captured antibodies were detected using PE-conjugated anti-mouse antibodies. Cells were analyzed by flow cytometry assay on a MACSQuant flow cytometer (Miltenyi).

Figure 7:
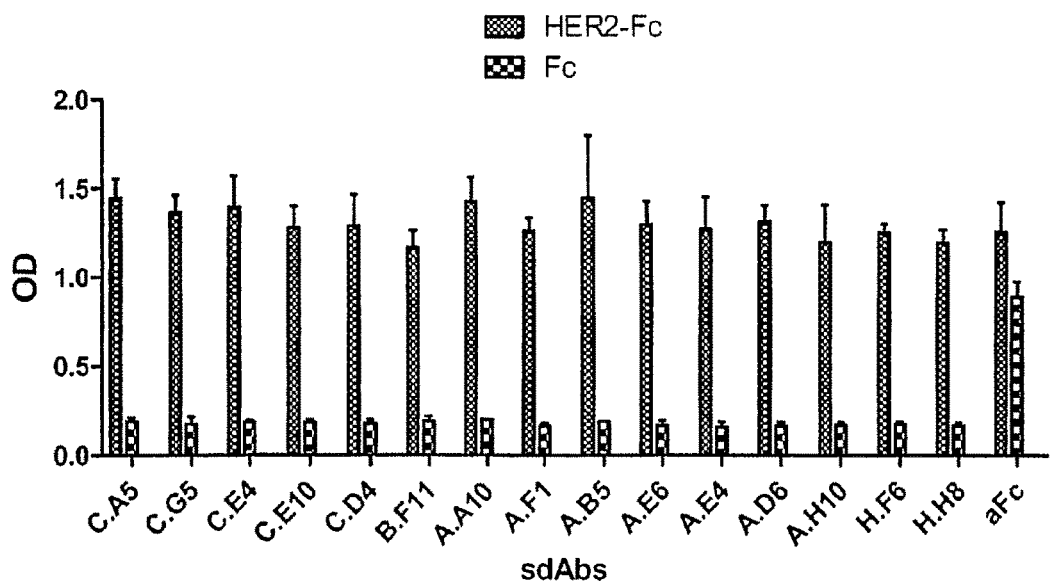

FIG. 7: Characterization of anti-HER2 sdAbs by ELISA. HER2-Fc recombinant fusion or human Fc portion were covalently immobilized on epoxy magnetic beads. Soluble sdAbs were incubated. After washing, bound sdAbs were detected using a HRP-labeled anti-6his mAb. aFc: anti human Fc sdAb used as positive control.

Figure 8A:
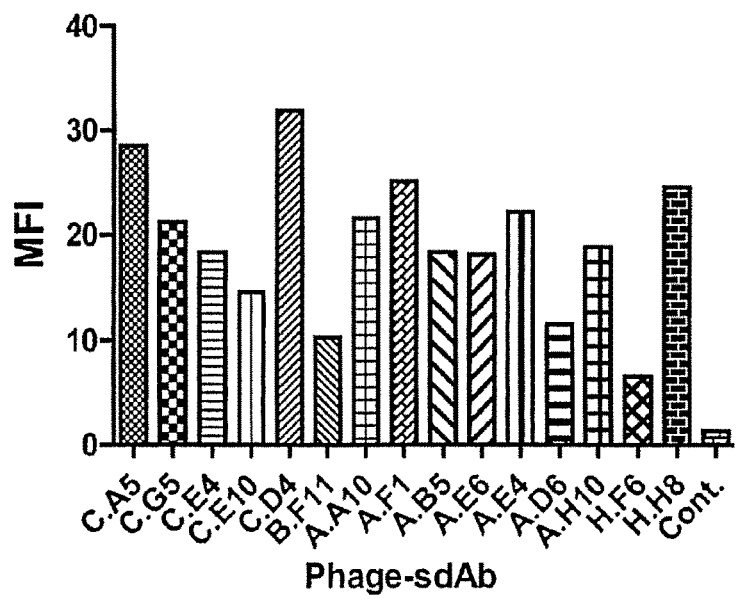
Figures 8B, 8C:
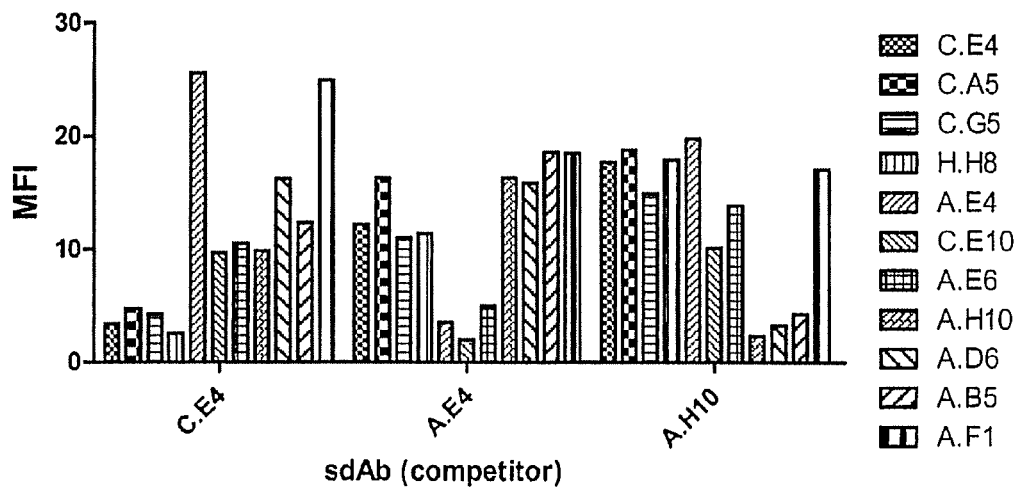

FIG. 8A-C: Characterization of anti-HER2 binders by flow cytometry. A) All selected phage-sdAbs were incubated with HER2+SKOv3 cells. After washing, bound phage were detected using PE-conjugated anti-M13 mAb. Cells were analyzed by flow cytometry assay on a MACSQuant flow cytometer (Miltenyi). B) Competition flow cytometry assay. Cells were incubated with phage-sdAbs in the presence of an excess of soluble anti-HER2 sdAbs C.E4, A.E4 or A.H10. Bound phage were detected as in A). C) Phage-sdAbs and sdAbs able to compete (sharing overlapping epitopes) were classified into groups.

EXAMPLE

Material & Methods

Cells Lines, Biopsies

MCF7, SK-BR-3 and T47D are a kind gift of Daniel Olive. MDA-MB-231 and HCC1937 are a kind gift of Marie Alix Poul (IRCM, Montpellier). BrCa-Mz-01, HCC1806, HCC1954 and BT474 are a kind gift of Jean Imbert (INSERM, U928, TAGC, Marseille, France). Cells lines MC38, MDA-MB-231, MCF7, T47D, HCC1937, HEK293T were cultured in DMEM complemented with 10% (v/v) fetal calf serum. Cells lines SK-BR-3, HCC1954, BrCaMz01, BT474 and HCC1806 were cultured in RPMI complemented with 10% (v/v) fetal calf serum. HME1 cell line was purchased from ATCC and grown as recommended by the manufacturer. All cell lines were grown at 37° C. in a humidified atmosphere and with 5% $CO_2$. PBMC are patient's donor cells. For transfection assay, HEK/293T were tranfected with Lipofectamine (Invitrogen), following the recommendation of the manufacturer.

Breast cancer biopsies (5801, 5772e, 5766, 5586, 5572i, 5592, 5011, 5712, 5713, 5033, 5627 kind gift of S. Garcia, CRCM, Marseille) or cells were lysed with a potter in lysis buffer: 150 mM NaCl, 1% Triton X-100, 50 mM Tris-HCl pH8 with protease inhibitor cocktail (Complete, Roche). The lysate was centrifuged for 10 min at 13000 g at 4° C. Supernatant was the final cell lysate. Total protein concentration (average between 2-5 mg/ml) was determined spectrophotometrically using a protein assay kit (Bio-Rad Laboratories, Hercules, Calif., USA).

Production and Purification of sdAbs

For polyclonal production of sdAbs from, 10 µl of output from selection round 1 and 2 were used to inoculate 200 ml of 2YT/ampicillin (100 µg/mL). Cells were grown at 37° C. (250 rpm) until the $OD_{600}$ reached 0.5. sdAb expression was induced by the addition of 0.1 mM IPTG (isopropyl-h-D-thiogalactopyranoside) at 30° C. (250 rpm) for 20 h.

sdAbs were purified by metal affinity chromatography as described [19].

In vitro Biotinylation

The in vitro biotinylation of protein was performed using Ez-link micro NMHS-PEO4-biotinylation kit (Perbio science) following the recommendation of the manufacturer.

Llama Immunization and Library Construction

Three young adult llama (Lama glama) were immunized subcutaneously at days 1, 30, 60, 90 and 120 with breast cancer biopsy lysate (two llamas) or with healthy breast biopsy (one llama). One llama was immunized with HER2-Fc protein and HEK-mGluR4 cells.

VHH library constructions were performed as described [13, 20]

Selection of Phage-sdAbs

To produce phage-sdAb library, 10 µL of the library was grown in 50 mL of 2YT/ampicillin (100 µg/mL)/glucose (2%) at 37° C. to an $OD_{600}$ of 0.5. Then, the culture was infected with KM13 or Hyperphage (Progen biotechnik) helper phage with a ratio of 20 phage/cell for 30 min at 37° C. without shaking. The culture was centrifuged for 10 min at 3000 g. The bacterial pellet was resuspended in 250 mL of 2YT/ampicillin (100 µg/mL)/kanamycine (25 µg/mL), and incubated overnight at 30° C. with shaking (250 rpm). Twenty five mL were then centrifuged for 20 min at 3000 g. Five mL of 20% PEG 6000, 2.5 M NaCl were added to the supernatant and incubated for 1 h on ice to precipitate phage particles. The solution was centrifuged for 15 min at 3000 g at 4° C. and the phage-containing pellet was re-suspended with 1 mL of PBS.

Different strategies of panning were performed. Some phages were selected using magnetic epoxy beads (Dynabeads, invitrogen) coated with antigen or lysates immobilized on epoxy beads during 48 h at 4° C. following recommendations of the manufacturer. Other phages were selected directly on cells ($2\times10^6$ cells). Beads or cells were washed three times in PBS (using a magnetic particle concentrator for magnetic beads and centrifugation step for cells) and phage-sdAb library (1 ml) and beads or cells were saturated in 2% milk PBS. For selection including a depletion step, phage-sdAb library were incubated with depletion support with rotation during 2 h at room temperature or at 4° C. for cells. Phage-sdAb libraries (depleted or not) were recovered and incubated with beads with rotation during 2 h at room temperature or at 4° C. for cells. For masked selection in the presence of soluble sdAbs, 10 µM of pure sdAbs were added during this step. Beads, cells or plate were washed 10 times with 1 ml 0.1% Tween PBS (without Tween for cells) and two times with PBS. Bound phage were eluted with tryspin solution (Sigma) at 1 mg/ml during 30 min at room temperature with rotation. Eluted phage were incubated without shaking with log-phase TG1 cells and plated on 2YT/ampicillin (100 µg/mL)/glucose (2%) in 15 cm Petri dishes. Some isolated colonies were grown overnight in microtiter plate containing 200 µL 2YT/ampicillin (100 µg/mL)/glucose (2%) and stored at −80° C. after the addition of 15% glycerol (masterplates). The remaining colonies were harvested from the plates, suspended in 2 mL 2YT/ampicillin (100 µg/mL)/glucose (2%) and used for phage production for the next round of selection.

Phage-sdAb ELISA on Epoxy Beads

A 96-well plate replicator was used to replicate the masterplates in 150 µL of fresh broth. Colonies were grown for 2 h at 37° C. under shaking (400 rpm) and 15 µL 2YT/ampicillin (100 µg/mL)/glucose (2%) containing $2\times10^9$ M13KO7 helper phage were added to each well and incubated for 30 min at 37° C. without shaking. The plate was centrifuged for 10 min at 1200 g and bacterial pellets were suspended in 150 µL 2YT/ampicillin (100 µg/mL)/kanamycine (25 µg/mL)1) and grown for 16 h at 30° C. under shaking (400 rpm). Phage-containing supernatants were tested for binding by ELISA.

Antigens HER2-Fc (R & D systems) or Fc were immobilized on magnetic epoxy beads (Dynabeads, invitrogen) during 48 h at 4° C. following recommendation of the manufacturer. For ELISA, 2 µl of beads/well was used. After three washes, beads were blocked with 5% milk-PBS (MPBS) for two hours at RT. Plates were incubated for 1 h at RT with 50 µl/well of phage-containing supernatants diluted at ½ in 4% MPBS. After three washes with 0.1% Tween PBS and three washes in PBS, plates were incubated with HRP-conjugated anti-M13 mAb (Pharmacia) diluted 1/5000 during 1 h at RT. After three washes with 0.1% Tween PBS and three washes in PBS, bound secondary antibodies were detected using ABTS. Coloration was followed at 405 nm.

Phage-sdAb ELISA with Lysate Coated on Plate

Fifty µl/well of biopsy mixture, or breast cancer cell lines (BT474, SK-BR-3, HCC1954, MCF7, MDA-MB-231, T47D, HCC1806, BRCA-Mz-01, HCC1937) or control cells HME1 and human PBMC lysates (200 µg/ml of total proteins) were coated overnight at 4° C. on maxisorp 96-well plate (Nunc). After three washes with PBS, plates were blocked with 5% MPBS for two hours at RT. For competitive assay, plates were incubated with 50 µl/well of sdAbs at 10 µg/ml during 1 h at RT. Plates were incubated for 1 h at RT with 50 µl/well of phage-containing supernatants diluted at ½ in 4% MPBS. After three washes with 0.1% Tween PBS and three washes in PBS, plates were incubated with HRP-conjugated anti-M13 mAb (Pharmacia) at 1/5000 during 1 h at RT. After three washes with 0.1% Tween PBS and three washes in PBS, bound secondary antibodies were detected using ABTS. Coloration was followed at 405 nm.

Phage-sdAb Flow Cytometry Assay

Experiments were performed on ice with rocking in 1% BSA PBS. Typically, $2\times10^5$ cells resuspended in 50 µl were distributed in 96-well microtiter plates. For competitive assay, plates were incubated with 50 µl/well of sdAbs at 10 µg/ml during 1 h at 4° C. Fifty µl/well of phage-containing supernatants diluted at ½ in 2% BSA PBS were added and plates were incubated for 1 h at 4° C. with. After three washes in PBS, plates were incubated with PE-conjugated anti-M13 mAb at 1/200 during 1 h at 4° C. After three washes in PBS, fluorescence was measured using a MACSQuant (Miltenyi) and results were analyzed with the MACSQuant software. Negative (secondary antibody only) controls were carried out.

HTRF Assay

A 96-well plate replicator was used to replicate the masterplates in 150 µL of fresh broth. Colonies were grown for 2 h at 37° C. under shaking (900 rpm) and 15 µL 2YT/ampicillin (100 µg/mL)/containing 0.1 mM IPTG were added to each well. The plate was incubated for 16 h at 30° C. with shaking (400 rpm). sdAb-containing supernatants were tested for binding by HTRF. To measure HTR-FRET signals, HEK cells were transfected plasmids coding for SNAP-tagged HER2 or mGluR4 receptors N-terminally fused to a SNAP tag 24 h prior to the assay (plasmids were a kind gift of Cisbio Bioassays and Jean-Philippe Pin (IGF, Montpellier), respectively). Cells were labeled with Tag-lite Snap-Lumi4-Tb, according to the manufacturer's kit protocol (Cisbio Bioassays). sdAb and D2 labeled anti-6his mAb (Cisbio) were added simultaneously. After incubation for 1 hour at RT, HTR-FRET signal (665 nm) and Lumi4-Tb donor signal (620 nm) were measured using a Tecan infinite M1000. HTRF ratio (665 nm/620 nm$\times 10^4$) was calculated to eliminate quenching and dispensing errors.

Immunohistochemistry Assay

In vitro biotinylated sdAbs were assayed in immunohistochemistry on 5 µm sections of paraffin-embedded cancer tissue. In addition, adjacent normal breast epithelium served as specificity control. A breast cancer tissue micro array containing 80 samples in duplicate (containing lobular and ductal breast cancer biopsies from grade I to III tumors with local lymph node invasion or not) and 14 samples healthy breast tissues in duplicate was also used. After deparaffinization of paraffin-embedded tissues, antigen retrieval of paraffin-embedded tissues was performed in 95° C. prewarmed citrate buffer during 20 min. Endogenous peroxidase activity was blocked by incubation with 3% $H_2O_2$. Slides were incubated for 1 h with in vitro biotinylated sdAbs at 10 µg/ml at room temperature and washed. Detection was performed by incubations at room temperature 30 min streptavidin peroxidase. Finally, visualization was performed by a DAB revelation (Dako) peroxidase reaction with haematoxylin as counterstain.

Results

1. Selection of Phage Antibodies against a Specific Part of Recombinant Protein Her2-Fc.

The proof of principle of this new approach was first established on a simple selection procedure using a purified recombinant protein. A single-domain antibody (sdAb) library was built using PBMCs of llamas immunized with various recombinant proteins consisting of fusion between ectodomains of relevant tumor markers and human IgG1 Fc portion including HER2-Fc and HER4-Fc. The aim of this first part of the study was to favor the selection of HER2 binders compared to Fc binders.

A basic strategy (i.e. direct selection of phage antibody produced using helper phage KM13) was compared to conventional depletion strategies on irrelevant Fc bearing molecules prior to positive selection on HER2-Fc fusion. A third approach was developed using Hyperphage to produce the phage-antibody particles since it was demonstrated that this helper phage can significantly increase the percentage of phage actually displaying an antibody fragment and the number of antibody fragment displayed per particles (valency). Theoretically, these two factors should increase the efficiency of the depletion strategy. Finally a masked selection strategy was performed. This approach consisted in a first selection of the library against a human IgG Fc portion. The selected clones were then polyclonally produced as soluble sdAbs which were added in excess during a second selection against recombinant fusion protein HER2-Fc to block their corresponding epitopes on the Fc portion. FIG. 1A shows that the direct selection strategy yielded a majority of Fc binders. The proportion of Fc binders was significantly reduced using a depletion step (with both helper phages). Interestingly, the vast majority of binders obtained by masked selection were HER2 ectodomain binders. Sequencing of the various outputs revealed 8 different clones out of 24 binders for the classical selection and 14 different clones out of 70 binders for the masked selection, suggesting that the masked selection on purified antigen could greatly improve the frequency of relevant binders without markedly impacting the output diversity.

2. Selection of Phage-antibodies against Specific Receptors on Transfected Cells Some targets, including for example members of the seven transmembrane receptors, cannot easily be recombinantly produced as soluble protein. In such cases, phage display can be used to select relevant binders by using a positive selection on transfected cells following a depletion step on the untransfected cell line. We decided to compare the efficiency of depletion vs. masked selection for the selection of binders against HER2 and mGluR4, a member of the metabotropic G-protein-coupled glutamate receptor family. For these experiments, we used a sdAb library that had been generated after immunization with transfected cells expressing HER2 and mGluR2. The two receptors were differentially expressed at the surface of HEK293T cells (HEK), as shown in FIG. 6A and B, using an anti-Flag tag antibody for detection. Masking sdAbs were obtained by two rounds of selection on untransfected HEK cells.

Figure 1B:
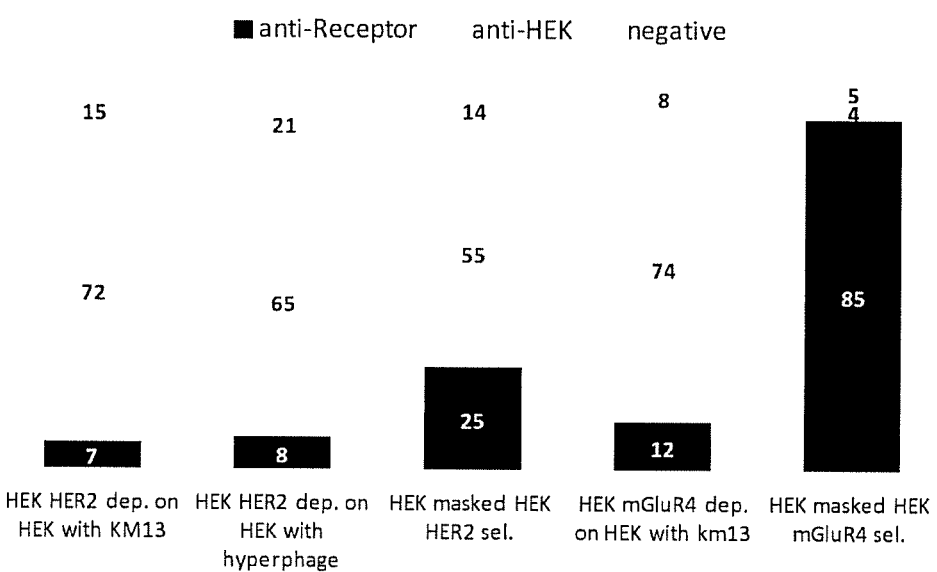

The output of depletion strategies were mainly constituted by HEK binders, and yielded only 7 and 8% of HER2 binders for KM13 and Hyperphage based approaches respectively, demonstrating a limited effect of the depletion strategy, even in high display conditions due to the use of hyperphage (FIG. 1B). The masked selection approach significantly improved the output since 26% of this output was constituted by HER2 binders.

Sequencing of a subset of the positive clones revealed 6 different clones out of 15 HER2 binders obtained by the two depletion strategies and 5 different clones out of 20 HER2 binders selected by masked selections. The dominant clone A.B5 was found in all different strategies. Several clones selected on purified antigens were not retrieved by cell selection. Conversely, clone H.H8 was only retrieved by masked selection on cells.

All 15 anti-HER2 binders obtained so far using recombinant antigen or transfected cells were produced as soluble fragments to be further characterized in terms of specificity and affinity.

Their specificity was first confirmed by ELISA. FIGS. 6A and B shows that all clones yielded a high signal on HER2-Fc and were negative against Fc, including sdAb H.H8. Next, flow cytometry on HER2 positive cells was used to demonstrate the ability of these anti-HER2 sdAbs to bind their antigen in a native context. All clones were found positive (FIG. 7), including 7 clones that were selected on recombinant antigen but not through cell selections. Flow cytometry competition experiments following the binding of phage-sdAbs in the presence of soluble sdAbs (FIG. 8B) could establish at least three groups of sdAbs binding to three independent HER2 epitopes, representing 11 clones (FIG. 8C).

A third independent approach based on Homogeneous Time Resolved Fluorescence (HTRF) was finally used to confirm the specificity and determine the affinity of anti-HER2 sdAbs. HEK cells were transfected with HER2 fused to the SNAP tag allowing a site-directed labeling of the receptor at the cell surface with a donor fluorophore. Bound sdAbs were detected using an anti-His tag monoclonal antibody labeled with an acceptor fluorophore. In this setting, the excitation of the donor fluorophore can lead to an emission of the acceptor fluorophore (FRET effect) if these two molecules are in close proximity, i.e. if the sdAb is binding to HER2. As shown in FIG. 2A, all anti-HER2 sdAbs were found positive in this assay whereas an irrelevant (anti-Fc) sdAb did not yield any signal. Three clones, binding overlapping epitopes yielded significantly lower FRET signal (A.E6, A.E4 and C.E10), suggesting that these epitopes are more distant to the SNAP tag than the other epitopes. H.F6 also yielded a lower signal, in agreement with flow cytometry results.

Dose response curves of the 12 best binders were used to determine the sdAb dissociation constants (FIG. 2B). The calculated $K_D$ values using a non-linear curve fitting program ranged between 0.5 and 7.3 nM (FIG. 2C).

To see if similar results could be obtained on a different type of receptors, depletion and masked selections were applied to the selection of sdAbs against the metabotropic glutamate receptor 4(mGluR4). This receptor belongs to the family of seven-transmembrane G protein-coupled receptor family and is difficult to produce recombinantly. Thus in this case, immunization, selection and screening steps were all performed using transfected HEK cells.

A conventional depletion step on HEK cells followed by a selection on mGluR4-transfected cells yielded a vast majority of HEK binders and less than 13% of mGluR4 binders (FIG. 1B), despite the high expression of the transfected receptor (FIGS. 6A and B). In sharp contrast, the masked selection strategy was highly successful since 90% of the output was specific for the relevant receptors and only 4% of the outputs were HEK binders (FIG. 1B).

The sequencing of 47 mGluR4 binders obtained by masked selection revealed 19 different clones, suggesting again this approach can lead to a good diversity of binders.

Soluble sdAbs corresponding to these 19 clones were produced and purified from E. coli for further characterization. As for HER2 binders, HTRF experiments were performed to establish their specificity for mGluR4. FIG. 3A shows that all clones yielded high HTRF signals demonstrating their specificity for mGluR4. In contrast, an irrelevant anti-Fc sdAb was found negative. Dose response curves and non-linear curve fitting analysis of seven best binders (FIG. 3B) were used to determine their dissociation constants. $K_D$ values of these monovalent single domain antibodies ranged from 0.3 to 9.3 nM (FIG. 3C).

3. Selection of Phage Antibodies with Breast Cancer Specificity

The efficiency of masked selection being established on transfected HEK cells, we applied this approach to the selection of binders against unknown antigens overexpressed in cancer samples. Llamas were immunized with breast cancer biopsies and the resulting sdAb libraries were selected against several samples.

Selection on breast cancer biopsy lysates: Selections were performed on a mixture of breast cancer biopsy lysates using a lysate of human peripheral blood mononuclear cells mixed to a lysate of normal human mammary epithelium cell line HME1(immortalized by hTERT expression) as normal sample. A basic approach using only depletion was compared to an approach using depletion plus masking using sdAbs selected from the same library by panning on the normal sample, and using KM13 or hyperphage as helper phage.

Ninety six clones were picked after two rounds of selection for each approach and a phage ELISA screening procedure using plastic-adsorbed lysates was performed to evaluate the specificity of the selected binders. The depletion strategy yielded 13% and 9% of clones showing specificity for the biopsy lysates, for KM13 or Hyperphage respectively. The addition of the masking procedure massively decreased the number of non cancer specific clones increased the proportion of cancer-specific clones to 40% and 30% for KM13 and hyperphage respectively. Sequencing of biopsy lysate binders revealed 9 different sequences including a highly dominant clone. Competition experiments performed by phage ELISA in the presence of an excess of each purified sdAb indicated that 4 of these clones were sharing a common epitope. A representative clone of this family and the 5 other sdAbs targeting independent epitopes were chosen for further characterization.

To confirm the specificity of these sdAbs for breast cancer, phage ELISA was performed on a panel of immobilized lysates from 11 different breast cancer biopsies, and on a mixture of breast cancer cell line lysates (see material and methods). Lysates of PBMCs and HME1 cell line were used as normal samples. This experiment confirmed the absence of signals on normal samples for all tested clones. Various binding profiles were generated against the 11 breast cancer biopsy lysates (FIG. 4A). To further confirm the cancer specificity of these antibody fragments, they were produced as soluble fragments and tested by immunohistochemistry. Out of the 6 tested sdAbs, only sdAb J.H6 yielded a strong signal on paraffin embedded tissue. This sdAb was thus further characterized on larger scale using breast cancer tissue microarray including 80 breast cancer samples (lobular and ductal breast cancer biopsies) and 14 healthy breast samples. None of the normal samples were stained by the sdAb and 75% of breast cancer biopsies were positive (FIG. 4C). FIG. 4B shows results on representative samples (cancer biopsies and normal samples).

Selection for cell surface binders on breast cancer cell lines: While intracellular cancer specific antigens can be useful as biomarkers for diagnosis purposes, they are not compatible with some therapeutic approaches such as therapeutic antibodies. For these approaches, the identification of cancer-specific membrane antigens is required. To evaluate the potential of masked selection in this case, and using the same sdAb library, we compared the output of two rounds of selection performed on a mixture of 4 different breast cancer cell lines (MDA-MB-231, MCF7, SKBr3, HCC1954) using a simple depletion step on a mixture of human PBMCs and normal breast epithelial cell line HME1 (PBMC+HME1), or a combination of deletion and masking using sdAbs from the same library selected on PBMC+HME1. Ninety six clones from each selection were screened as phage-sdAb by flow cytometry on the mixture of breast cancer cell lines and normal sample.

A simple depletion did not lead to any cancer specific clones. 60% and 35% of tested clones were positive on PBMC+HME1 for KM13 and hyperphage respectively. The addition of the masking step very efficiently blocked the selection of such binders since only 1 or 2 clones out of 96 were positive on PBMC+HME1. Interestingly, 6 and 12 clones were found positive on the mixture of breast cancer cell lines, for KM13 and hyperphage respectively. Sequencing of these binders revealed 11 different sequences. Flow cytometry competition experiments performed using purified sdAbs indicated that six different epitopes were targeted by these 11 different sdAbs. A representative binder of each epitope was chosen for further studies.

The six purified sdAbs were tested by flow cytometry against 6 different breast cancer cell lines, 7 other cancer cell lines of various origins, against normal breast epithelial cell line HME1 and against human PBMCs. As shown in FIG. 5A, none of the sdAbs were positive on normal cells. Four sdAbs (M.C9, M.B9, M.H3, M.H12) were strongly positive against most tested cancer cell lines. sdAbs M.D5 was only positive on two breast cancer cell lines whereas sdAb M.A4 was positive on one breast cancer cell line (MDA-MB-231) as well as on PC3(prostate cancer) and HeLa (cervical cancer) cell lines.

Immunohistochemistry characterization demonstrated that two of these sdAbs (M.H3, M.H12) were functional on paraffin embedded tissues. These sdAbs were then assayed on breast cancer tissue micro array. FIG. 5B displays representative results obtained with these two sdAbs. None of the 14 normal samples were stained by these two sdAbs and 98% or 79% of breast cancer biopsies were strongly stained by sdAb M.H3 and M.H12, respectively (FIG. 5C).

Discussion

We have designed a new procedure to focus the output of a phage display toward specific epitopes of a chimeric protein, toward transfected membrane receptors and toward specific or overexpressed cancer markers using crude lysates or intact cells when surface markers are preferred. In all cases, the principle of masking non relevant epitopes was shown to be more efficient than conventional depletion. The general concept underlying this approach is merely to block unwanted epitopes using the addition of an excess of binders previously selected from the very same library by panning against the non relevant sample.

This simple procedure is very powerful because it takes advantage of the potential biases of a library. Indeed, libraries often contain a large number of binders directed against non relevant but highly abundant or very immunoreactive epitopes. These binders often outcompete relevant binders against low abundant epitopes when selections are performed on complex samples. Masked selection should be very efficient in this case because these dominant binders targeting abundant proteins would be very efficiently selected. By this process, the polyclonal population of soluble binders selected on the non-relevant sample (the mask) will be enriched for binders that have to block the most problematic (abundant and/or immunoreactive) epitopes.

Our results demonstrate some efficiency of depletion strategies but also highlight their shortcomings in difficult selections on complex samples. The principle of depletion relies on the capture of non relevant binders from the phage population before positive selection. This approach can improve the specificity of an output but cannot be totally efficient since, as for any non covalent interaction, a fraction of the total phage-antibody to be depleted will stay in solution at a ratio dependent on the affinity of the antibody. Increasing the number of pIII fused to an antibody fragment using for example hyperphage as helper phage should increase the apparent affinity of binders and thus increase the proportion of bound phage during the depletion step. Such an effect could be seen in this study on depletion performed on Fc portion but was not visible on selections performed on complex samples. Other techniques have been proposed to focus a phage selection on a particular antigen including guided selection [17, 18] and competitive elutions [7]. These techniques have been successfully used in several studies but they are limited in several aspects. Guided selection depends on the availability of a cloned antibody and is labor-intensive. Competitive elution uses a known ligand or monoclonal antibody to specifically elute phage-antibodies binding to the same epitopes. Unfortunately this strategy naturally favors the selection of low affinity binders and cannot be used for target discovery.

On the other hand, the masked selection is based on a competition between masking antibody fragments and phage particles. The input of a selection procedure usually contains $10^{12}$ phage particle in 1 mL, leading to a phage concentration of around 2 nM. Single domain antibodies are easily produced in *E. coli* and we routinely use 10 µM of polyclonal sdAbs for the masking procedures, ensuring a huge excess of sdAbs over phage-sdAbs to guarantee an efficient blocking of non relevant epitopes. This process does not influence the affinity of selected binders and as shown in this study, it can efficiently leads to the selection by binders against unknown but differentially expressed targets.

In principle, this technique is very flexible and can be used with any kind of antibody fragments (scFv, Fab fragments), alternative scaffolds (darpins, monobodies, affibodies, anticalins As described in this work, masked selection can be used to select binders against unknown targets that can be subsequently identified by immunoprecipitation and mass spectrometry analysis for example and has a great potential for cancer therapy. It should also be of high interest for many other purposes, such as the identification of specific cell surface receptors of some cell types, such as normal and cancer stem cells or regulatory T cells for example.

REFERENCES

Throughout this application, various references describe the state of the art to which this invention pertains. The disclosures of these references are hereby incorporated by reference into the present disclosure.

1. Kohler G, Milstein C: Continuous cultures of fused cells secreting antibody of predefined specificity. Nature 1975, 256:495-497.
2. McCafferty J, Griffiths A D, Winter G, Chiswell D J: Phage antibodies: filamentous phage displaying antibody variable domains. Nature 1990, 348:552-554.
3. Weiner L M: Fully human therapeutic monoclonal antibodies. J Immunother 2006, 29:1-9.
4. Hoogenboom H R: Selecting and screening recombinant antibody libraries. Nat Biotechnol 2005, 23:1105-1116.
5. Ngai P K, Ackermann F, Wendt H, Savoca R, Bosshard H R: Protein A antibody-capture ELISA (PACE): an ELISA format to avoid denaturation of surface-adsorbed antigens. J Immunol Methods 1993, 158:267-276.
6. Siva A C, Kirkland R E, Lin B, Maruyama T, McWhirter J, Yantiri-Wernimont F, Bowdish K S, Xin H: Selection of anti-cancer antibodies from combinatorial libraries by whole-cell panning and stringent subtraction with human blood cells. J Immunol Methods 2008, 330: 109-119.
7. Veggiani G, Ossolengo G, Aliprandi M, Cavallaro U, de Marco A: Single-domain antibodies that compete with the natural ligand fibroblast growth factor block the internalization of the fibroblast growth factor receptor 1. Biochem Biophys Res Commun 2011, 408:692-696.
8. Stefan N, Martin-Killias P, Wyss-Stoeckle S, Honegger A, Zangemeister-Wittke U, Pluckthun A: DARPins recognizing the tumor-associated antigen EpCAM selected by phage and ribosome display and engineered for multivalency. J Mol Biol 2011, 413:826-843.
9. Liew P X, Ge F, Gullo C, Teoh G K, Hwang W Y: Use of phage display to isolate specific human monoclonal antibody fragments against a potential target for multiple myeloma. Ann Acad Med Singapore 2009, 38:621-629.
10. Omidfar K, Rasaee M J, Modjtahedi H, Forouzandeh M, Taghikhani M, Golmakani N: Production of a novel camel single-domain antibody specific for the type III mutant EGFR. Tumour Biol 2004, 25:296-305.
11. Mazuet C, Lerouge D, Poul M A, Blin N: Breast carcinoma specific antibody selection combining phage display and immunomagnetic cell sorting. Biochem Biophys Res Commun 2006, 348:550-559.
12. Nielsen U B, Marks J D: Internalizing antibodies and targeted cancer therapy: direct selection from phage display libraries. Pharm Sci Technolo Today 2000, 3:282-291.
13. Behar G, Chames P, Teulon I, Cornillon A, Alshoukr F, Roquet F, Pugniere M, Teillaud J L, Gruaz-Guyon A, Pelegrin A, Baty D: Llama single-domain antibodies directed against nonconventional epitopes of tumor-associated carcinoembryonic antigen absent from nonspecific cross-reacting antigen. FEBS J 2009, 276:3881-3893.
14. Roovers R C, van der Linden E, de Bruine A P, Arends J W, Hoogenboom H R: Identification of colon tumour-associated antigens by phage antibody selections on primary colorectal carcinoma. Eur J Cancer 2001, 37:542-549.
15. Jensen K B, Jensen O N, Ravn P, Clark B F, Kristensen P: Identification of keratinocyte-specific markers using phage display and mass spectrometry. Mol Cell Proteomics 2003, 2:61-69.
16. Geuijen C A, Bijl N., Smit R C, Cox F, Throsby M, Visser T J, Jongeneelen M A, Bakker A B, Kruisbeek A M, Goudsmit J, de Kruif J: A proteomic approach to tumour target identification using phage display, affinity purification and mass spectrometry. Eur J Cancer 2005, 41:178-187.
17. Beiboer S H, Reurs A, Roovers R C, Arends J W, Whitelegg N R, Rees A R, Hoogenboom H R: Guided selection of a pan carcinoma specific antibody reveals similar binding characteristics yet structural divergence between the original murine antibody and its human equivalent. J Mol Biol 2000, 296:833-849.

18. Figini M, Obici L, Mezzanzanica D, Griffiths A, Colnaghi M I, Winter G, Canevari S: Panning phage antibody libraries on cells: isolation of human Fab fragments against ovarian carcinoma using guided selection. Cancer Res 1998, 58:991-996.

19. Even-Desrumeaux K, Baty D, Chames P: Strong and oriented immobilization of single domain antibodies from crude bacterial lysates for high-throughput compatible cost-effective antibody array generation. Mol Biosyst 2010, 6:2241-2248.

20. Alvarez-Rueda N, Behar G, Ferre V, Pugniere M, Roquet F, Gastinel L, Jacquot C, Aubry J, Baty D, Barbet J, Birkle S: Generation of llama single-domain antibodies against methotrexate, a prototypical hapten. Mol Immunol 2007, 44:1680-1690.

The invention claimed is:

1. A method for selecting a plurality of binders specific for a cell comprising i) building a binder library by using peripheral blood mononuclear cells (PBMCs) obtained from at least one animal immunized with the cell or a cell lysate, ii) producing a phage binder library by infecting the binder library of step i) with a helper phage, iii) performing with the phage binder library of step ii) at least one round of selection against a second cell or second cell lysate, iv) producing soluble binders with selected clones obtained at step iii), v) performing with the phage binder library of step ii) at least one round of selection against the cell in the presence of an excess of binders produced by step iv), and vi) cloning and recovering the binders from the clones selected at step v).

2. The method of claim 1, further comprising sequencing the binders from the clones selected at step vi).

* * * * *